US011766555B2

(12) United States Patent
Matthes et al.

(10) Patent No.: US 11,766,555 B2
(45) Date of Patent: Sep. 26, 2023

(54) CONNECTING DEVICE

(71) Applicant: Berlin Heart GmbH, Berlin (DE)

(72) Inventors: Michael Matthes, Atlandsberg (DE); Heiko Gundlach, Berlin (DE); Nedim Arslan, Berlin (DE); Gerhard Lauterbach, Berlin (DE); Daniel Phillips, Berlin (DE); Kim Peter Winterwerber, Berlin (DE)

(73) Assignee: Berlin Heart GmbH, Berlin (DE)

( * ) Notice: Subject to any disclaimer, the term of this patent is extended or adjusted under 35 U.S.C. 154(b) by 1479 days.

(21) Appl. No.: 15/977,573

(22) Filed: May 11, 2018

(65) Prior Publication Data
US 2018/0256799 A1 Sep. 13, 2018

Related U.S. Application Data

(63) Continuation of application No. PCT/EP2016/072664, filed on Sep. 23, 2016.

(30) Foreign Application Priority Data

Nov. 25, 2015 (EP) .................................... 15196333

(51) Int. Cl.
A61M 60/148 (2021.01)
A61M 60/178 (2021.01)
(Continued)

(52) U.S. Cl.
CPC ..... *A61M 60/148* (2021.01); *A61B 17/12136* (2013.01); *A61M 60/178* (2021.01);
(Continued)

(58) Field of Classification Search
CPC .. A61M 60/268; A61M 60/857; A61M 60/86; A61M 60/863; A61M 60/896;
(Continued)

(56) References Cited

U.S. PATENT DOCUMENTS 6,319,231 B1* 11/2001 Andrulitis ........... F16L 37/0885
623/3.26
7,942,805 B2 5/2011 Shambaugh, Jr.
(Continued)

FOREIGN PATENT DOCUMENTS

CN 102458680 A 5/2012
CN 103608050 A 2/2014
(Continued)

OTHER PUBLICATIONS

Chinese First Notification of Office Action with English translation, issued in CN Application No. 201680068335.4, dated Jul. 3, 2020, pp. 1-20, Chinese Intellectual Property Administration, Beijing, China.
English translation of International Search Report, issued in International Application No. PCT/EP2016/072664, dated Dec. 1, 2016, pp. 1-3, European Patent Office, Rijswijk, The Netherlands.

*Primary Examiner* — Brooke Labranche
*Assistant Examiner* — Lauren Dubose
(74) *Attorney, Agent, or Firm* — Crowell & Moring LLP

(57) ABSTRACT

A connecting device is provided for connecting a pipe or tube-shaped element to the heart or a blood vessel of a patient, comprising a suture ring that has an opening, which can be closed by means of a closure element and through which said pipe or tube-shaped element is guided in the axial direction. The closure element is secured to the suture ring by means of at least one elastic securing element. A radially-expandable sealing element can also be provided in order to establish a sealing placement of the closure element against the suture ring.

11 Claims, 5 Drawing Sheets

(51) Int. Cl.
*A61M 60/861* (2021.01)
*A61M 60/859* (2021.01)
*A61B 17/12* (2006.01)
*A61M 60/216* (2021.01)
*A61B 17/22* (2006.01)

(52) U.S. Cl.
CPC ........ *A61M 60/216* (2021.01); *A61M 60/859* (2021.01); *A61M 60/861* (2021.01); *A61B 2017/22048* (2013.01)

(58) Field of Classification Search
CPC .............. A61M 60/148; A61M 60/859; A61M 60/178; A61M 60/216; A61M 60/861; A61M 39/00; A61M 39/0208; A61M 2039/0223; A61M 2039/0288; A61M 60/00; A61M 39/20; A61M 39/0247; A61M 2039/0282; A61F 5/0056; A61B 2017/342; A61B 17/12136; A61B 2017/22048; A61B 2017/3425; A61B 17/0057; A61B 17/0644; A61B 2017/00243; A61B 2017/00247
USPC ........................................................ 403/321
See application file for complete search history.

(56) References Cited

U.S. PATENT DOCUMENTS

| | | | |
|---|---|---|---|
| 8,590,749 B2 | 11/2013 | Beranger et al. | |
| 9,486,565 B2 | 11/2016 | Göllner et al. | |
| 2012/0296358 A1* | 11/2012 | Nguyen | A61B 17/11 606/170 |
| 2013/0012926 A1* | 1/2013 | Goellner | F16L 33/28 604/535 |
| 2013/0211248 A1* | 8/2013 | Cowan | A61M 5/1452 600/432 |
| 2014/0316426 A1 | 10/2014 | Göllner et al. | |
| 2015/0273124 A1* | 10/2015 | Callaway | A61M 60/857 623/3.26 |

FOREIGN PATENT DOCUMENTS

| | | |
|---|---|---|
| CN | 103945876 A | 7/2014 |
| CN | 203724137 U | 7/2014 |
| WO | WO 00/47270 | 8/2000 |
| WO | WO 2009/085243 | 7/2009 |
| WO | WO 2014/144085 | 9/2014 |
| WO | WO 2015/134944 A1 | 9/2015 |

* cited by examiner

CONNECTING DEVICE

CROSS-REFERENCE TO RELATED APPLICATIONS

This application is a continuation of PCT/EP2016/072664 filed Sep. 23, 2016, which claims priority under 35 USC § 119 to European patent application EP 15196333.7 filed Nov. 25, 2015. The entire contents of each of the above-identified applications are hereby incorporated by reference.

TECHNICAL FIELD

The invention lies in the field of mechanical engineering and mechanics and can be used particularly advantageously in the field of medical technology.

BRIEF DESCRIPTION OF THE DRAWINGS

FIG. 5b shows a spring ring as a detail from FIG. 5a;

DETAILED DESCRIPTION

Figure 1:
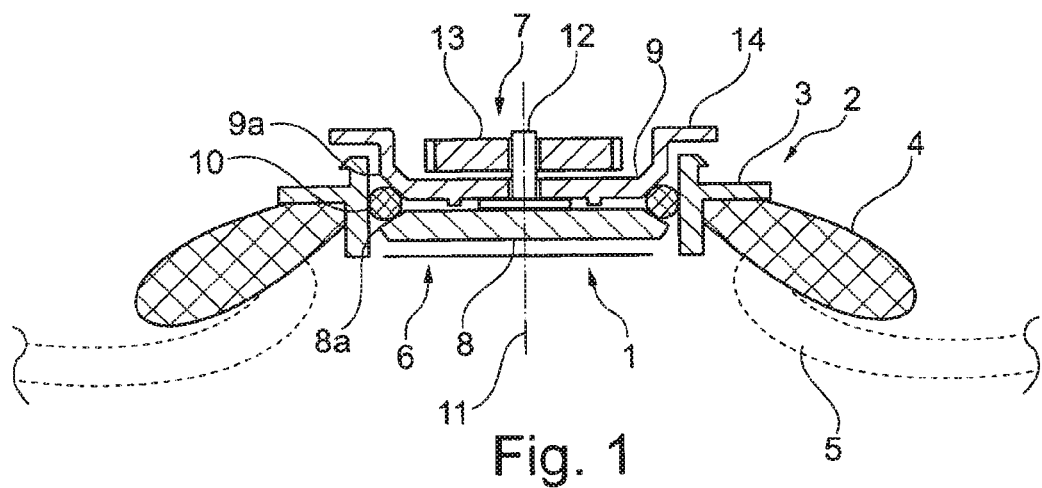
FIG. 1 shows a schematic section of a connecting device with a ring seal, which serves as a securing element and as a sealing element.

More specifically, the invention relates to a connecting device, with which pipe or tube-shaped elements can be connected to a cavity, in particular a heart or blood vessel in a patient's body. Such tasks are performed for example in the case of temporary or permanent connection of a pump to a blood vessel or directly to a heart of a patient. In the case of applications of this kind, a cannula or a pump pipe can be directly secured to the wall of a heart or the wall of a vessel and can be guided through this wall in as fluid-tight a manner as possible.

For this purpose it is already known to use what are called suture rings, wherein a suture ring usually comprises a solid annular body, for example made of metal, and a flexible part, which is connected to said body and which can be secured by means of conventional securing methods to the organic tissue which surrounds the opening through which the pipe or tube passes. For example, this securing can be produced by sewing by means of a thread or gluing or welding. A pipe connection, a tube, or a cannula can then usually be guided through the suture ring in a sealed manner.

In some cases, the corresponding opening in the tissue is temporarily or ultimately no longer required, and it is therefore advantageous to close said opening. In some cases, it can be advantageous for this purpose to leave the suture ring on the tissue and to close the opening in the suture ring. In so doing, further damage to organic tissue is avoided, and the opening can be closed tightly at the suture ring if an appropriate closure mechanism is selected. There are then no uncertainties when it comes to connecting or closing organic tissue. In addition, the closed suture ring can also be opened again later without great effort.

What is known as a weaning stopper is known from the prior art, for example within the scope of U.S. Pat. No. 7,942,805 B2, which enables the closure of a suture ring. There, a closure element is secured from outside by means of a clamping ring ("weaning" denotes the process, in a patient after a treatment, of dispensing intermittently or ultimately with the assistance provided by a heart pump, such that the corresponding connector must be removed or closed.)

A connecting device is provided for connecting a pipe or tube-shaped element to the heart or blood vessel of a patient, where the connecting device allows an opening to be closed with minimal structural effort and in the most secure and reliable manner possible, wherein the effort involved in closing the opening should also be kept low and the procedure should be as gentle as possible for the patient.

The innovation consequently relates to a connecting device for connecting a pipe or tube-shaped element to the heart or blood vessel of a patient using a suture ring that has an opening, which can be closed by means of a closure element and through which said pipe or tube-shaped element is guided in the axial direction. The closure is secured to the suture ring by at least one elastic securing element.

By way of the elastic securing element, on the one hand, a closure element can be secured to a suture ring without great effort by means of a clamping device, and on the other hand, the securing element can also be used potentially at least in part as a sealing element due to its resilience. It is thus possible to secure the closure element to the suture ring without the suture ring having to be moved or manipulated to a great extent. The securing by the elastic securing element functions permanently and guarantees the mechanical retention of the closure element regardless of movements performed by the patient and changes to the ambient conditions. In particular, a connection by means of an elastic securing element is to be produced in a simple manner and without great stress on the patient, with minimal intervention in the patient's body. The closure element can be placed in a sealing manner against an end face of the suture ring or against an inner face, which in particular is cylindrical. It is generally also conceivable that the closure element is placed in a sealing manner against an outer peripheral face of the suture ring.

One embodiment of the innovation provides that the closure element has a sealing element sealing against the suture ring at the outer periphery of said closure element and also a device for expanding the sealing element in the radial direction of the suture ring. The sealing element is usually deformable, in particular elastically, and for example can consist of an elastomer or can comprise an elastomer. For example, it can also consist of a plastically deformable material having adhesive properties, typically an adhesive, or can be connected to the suture ring by means of an adhesive. For example, it can seal against a cylindrical or differently shaped inner face of the suture ring or against other faces of the suture ring, for example against an end face, a bevel, or in a groove of the suture ring, by tight abutment. The sealing element for example can be identical to the securing element or can be part of the securing element; however, it can also be provided independently of the securing element.

The sealing element can be solid or hollow, for example can be formed as a hollow body with a central cavity or also as a closed or open-pore foam material, or can comprise a foam material of this kind. It is possible (this is true for all embodiments of the present industrial right application), instead of a foam material, to also provide open-pore textile fabric to promote the growth of organic, in particular human tissue. This can comprise graft and/or velour material, for example.

The sealing element, the securing element, and the closure element can each consist wholly or partially of a metal or a plastics material, also of a foamed material, for example also metal foam formed of an open-pore metal structure. A potential metal here is titanium. The surfaces or surface regions can be (this is true for all elements mentioned in this paragraph) textured here in such a way that ingrowth is promoted. Textile fabric or other fabric with or without texturing can also be used.

Materials that are biocompatible and that are capable of ingrowth are generally possible materials for the aforesaid components.

A further solution within the scope of the present innovation can provide that the sealing element can be compressed in the axial direction and therefore can be expanded in the radial direction. This solution for example can provide that the sealing element consists of a non-volume-compressible elastomer and for example is annular, or also that the sealing element is or comprises a hollow elastomer element that can be deformed under compression of a medium disposed in the cavity.

Furthermore, it can be provided within the scope of the innovation that the closure element has a peripheral recess at its periphery for the sealing element compressible in the axial direction. For example, the closure element can comprise a disc-like or pot-like element, which at its periphery has a corresponding recess, which for example can be formed as a peripheral groove.

The outer contour of the closure element can be round, in particular circular, but can also be elliptical or quadrangular or polygonal, for example in each case with rounded corners. The term "radially" in this case means for example directed outwardly towards the periphery from the centroid of an area or centre point of an area.

An implementable solution can also provide that the closure element comprises at least two separate elements that can be pressed against one another in the axial direction and between which there is formed a radially outwardly open gap, in particular a peripheral groove at the periphery of the closure element, for receiving the sealing element. The closure element for this purpose can comprise two elements that are arranged one after the other in the axial direction, i.e. in the through-direction of the connecting device, and which are movable against one another in the axial direction, and between which there can be arranged a solid or hollow elastomer element as sealing element. The elements which can be pressed against one another can be formed for example as flat discs or spherical cap-like bodies, or one of the bodies can be formed as a disc and the other body can be formed as a ram that can be pressed against the disc. The sealing element can lie over the entire width between the two elements that can be pressed against one another or can be formed as an annular body.

In the event of axial pressing, the sealing element is expanded radially outwardly, until it contacts a sealing face of the suture ring and seals there. In a particular variant of the innovation, a peripheral groove for receiving the sealing element can be formed at the periphery of the closure element. The groove can be deformable in such a way that the width of the groove can be reduced in the axial direction, such that the sealing element can be pushed out of the groove and in the radial direction outwardly against the suture ring. This can be implemented for example in that the various side walls of the groove are formed by the various elements that can be pressed against one another.

In particular for the case that a radially outwardly peripheral groove is arranged on the closure element, it can also be provided that a peripheral and radially outwardly pointing bevel is formed at the base of the groove at least on one of the two elements that can be pressed against one another, and that in particular the base of the groove is V-shaped in cross-section, wherein each of the two limbs of the V-shaped base is formed by one of the elements. A shaping of this kind of the groove specifically requires the conversion of a compression of the sealing element in the axial direction into an expansion in the radial direction outwardly.

The two elements that can be pressed against one another can be pushed against one another axially by different mechanisms, for example in that one of the elements is placed against a stop of the suture ring and the second element is pressed against the first element by clamping elements which are supported on the suture ring. In order for the compression of the two elements that can be pressed against one another to be provided as easily as possible and without any movement of the suture ring or without any loading of the suture ring with forces, it can be provided for example that the two elements that can be pressed against one another are connected to one another by a central screw connection. Thus, only the two elements that can be pressed against one another have to be screwed to one another or to a third element, wherein either there are no forces at all on the suture ring or any such forces can be kept within narrow limits.

To this end, it can be provided specifically for example that at least one threaded pin passes through an opening in one of the elements that can be pressed against one another, without threaded engagement, and that at least one threaded nut can be screwed onto the threaded pin in order to press the elements of the closure element against one another. A screw connection of this kind on the one hand can be easily tensioned in order to compress the sealing element and on the other hand can be easily released again, for example in order to remove the closure element again. In addition, the force acting on the sealing element can be continuously adjusted by the screw connection. The thread of the screw connection should have such a fine pitch that the screw connection is self-locking.

Within the scope of the innovation it can also be provided that the two elements that can be pressed against one another have central threads engaging in one another and are rotatable relative to one another. In this case, one of the two elements that can be pressed against one another can comprise an external thread and the other element can comprise an internal thread, which are screwed to one another directly. These threads can be provided either in the region of the outer periphery of the closure element or also radially further inwardly on connections or pipe elements provided accordingly.

Generally, it can also be provided, for the case in which no thread is provided between the elements that can be pressed against one another, that the two elements that can be pressed against one another have a guide device for guiding their relative movement in the axial direction. This is important in particular when the axial pressing force is provided by clamping elements which themselves do not provide any guidance of the two elements that can be pressed against one another in the axial direction.

In any case, it can also be provided that a stop for limiting the relative movement of the two elements that can be pressed against one another in the axial direction is provided on the closure element. The compression of the sealing element in the axial direction is hereby limited, such that for example the risk of destruction of the sealing element or the risk that the sealing element will be fully pushed out from the gap between the elements that can be pressed against one another is limited.

An advantageous embodiment of the innovation can provide for example that the sealing element is an elastomer seal with in particular a circular, oval, triangular or quadrangular cross-section. The elastomer seal can consist for example of a rubber, a silicone elastomer, an open-pore textile fabric (for example a velour or graft material), or another comparable material, and for example can also be formed as a closed-pore or open-pore foam material or as a textured material. It is furthermore also possible that the elastomer seal has one or more cavities, which are filled with a fluid, a gel, or a gas, wherein the cavity can be closed and deformable. The filling of a medium into the cavity in order to deform the sealing element can also be provided.

To this end, a filling device which can be opened and closed can be provided for example on the sealing element. For example, a material that initially is flowable and the filling of which into the cavity leads to a radial expansion of the sealing element, wherein the material can be later cured or hardened in order to solidify the sealing element in the expanded state, can also be filled into the cavity of a sealing element of this kind. A material of this kind for example can also be injected into the cavity of a sealing element by means of an injection needle, without a separate filling device.

In this context, it should be noted that a possible embodiment of the innovation can provide that the sealing element is a deformable, in particular elastic hollow body, which can be filled with a gas, a liquid or a gel, in particular in torus or sphere form.

In principle, the connection device can also be formed in such a way that the closure element has a cavity surrounded by an elastic wall, which together with the elastic wall can be radially expanded by insertion of a dowel-like body or by expansion of an expansion element within the cavity. To this end, the closure element for example can comprise a sealing element in the form of a torus or a ring seal, into the axial through-opening of which a body widening in a dowel-like or conical manner is inserted, which body radially expands the toroidal body with respect to its axis of symmetry.

However, an expansion element which can be actuated from outside, such that the walls of the sealing element delimiting the cavity are expanded radially outwardly until they seal against a sealing face of the suture ring, can also be provided within the cavity of a sealing element.

Figure 2:
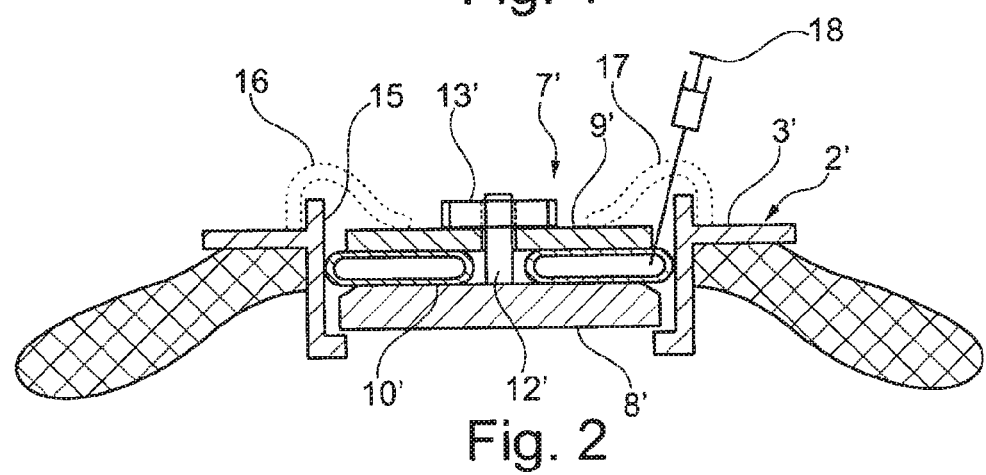
FIG. 2 shows a connecting device with a hollow ring seal.
Figure 3:
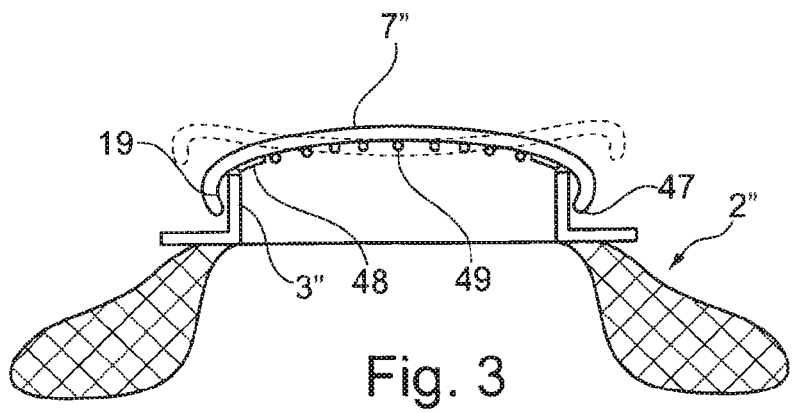
FIG. 3 shows a connecting device with an elastic cover.
Figure 4:
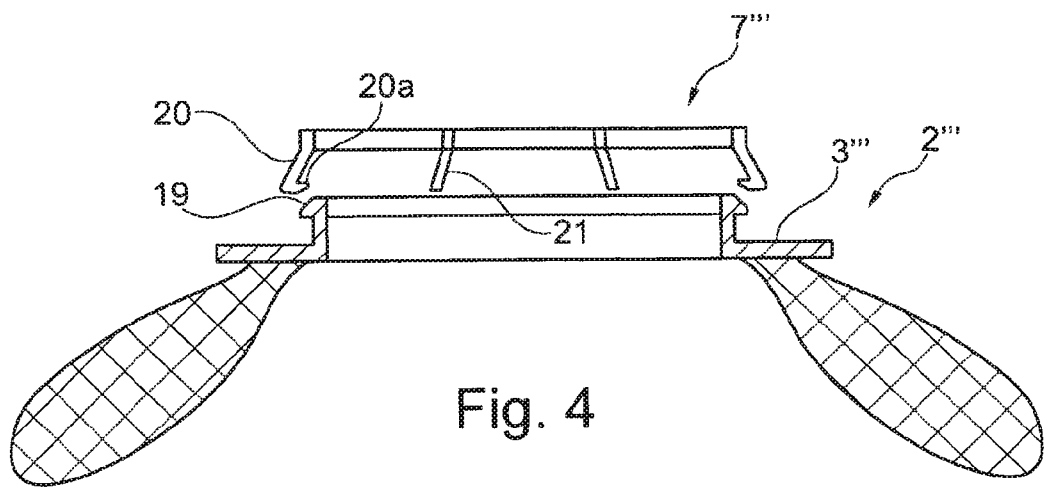
FIG. 4 shows a connecting device with a cover that has elastic hooks.
Figure 5A:
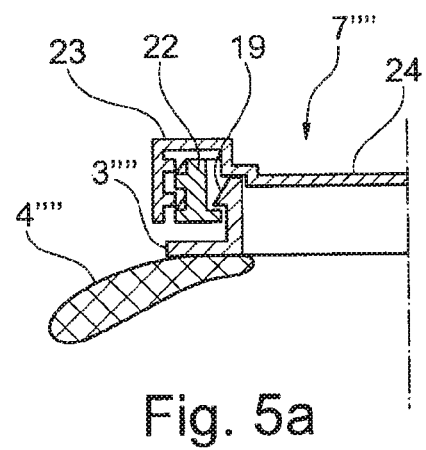
FIG. 5a shows, in a half-section, a connecting device with a cover and a cap nut.
Figure 5B:
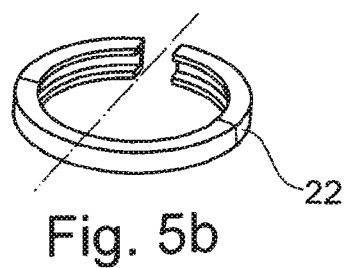
Figure 6:
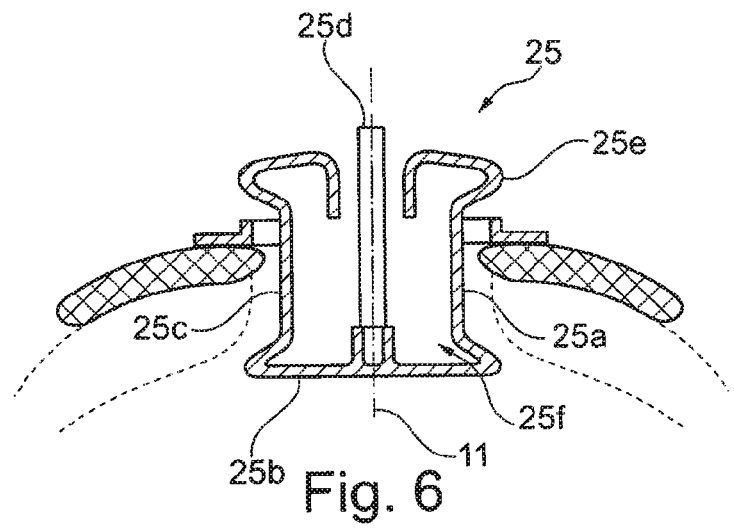
FIG. 6 shows, in section, a connecting device with a hollow rubber body.
Figure 7:
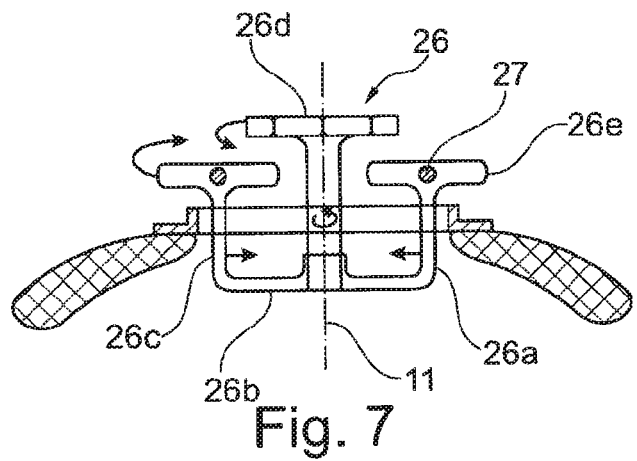
FIG. 7 shows a connecting device with a hollow rotatable rubber body.
Figure 8:
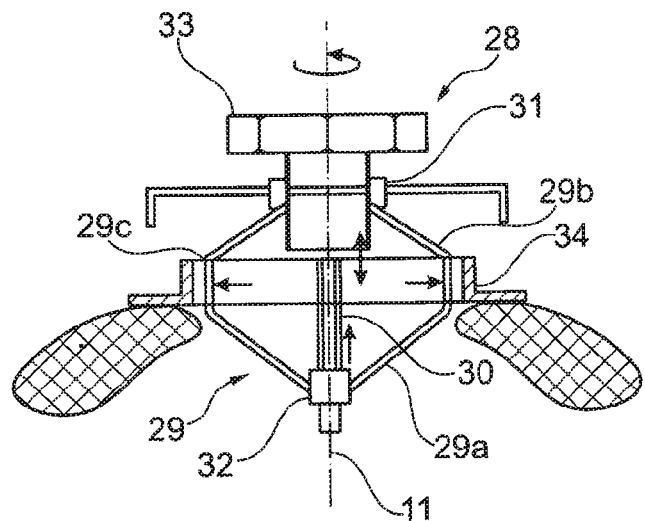
FIG. 8 shows a connecting device with a hollow sealing element and an expansion device.
Figure 9:
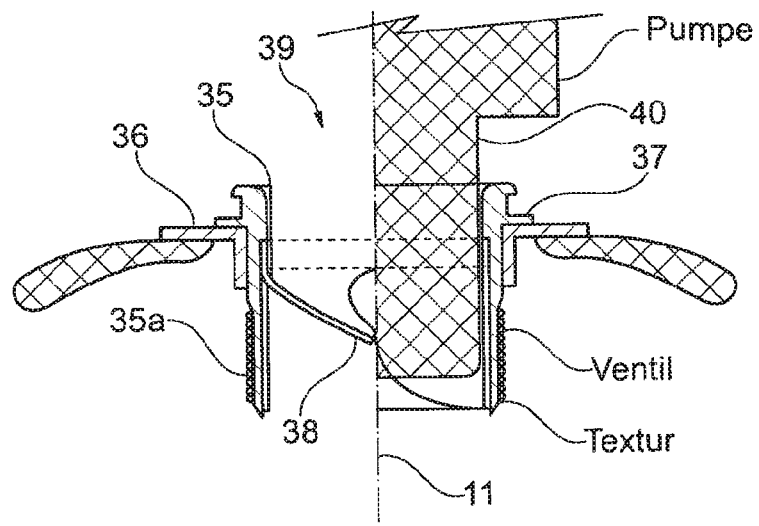
FIG. 9 shows a connecting device with a valve, on the right-hand side with an inserted pump pipe.
Figure 10:
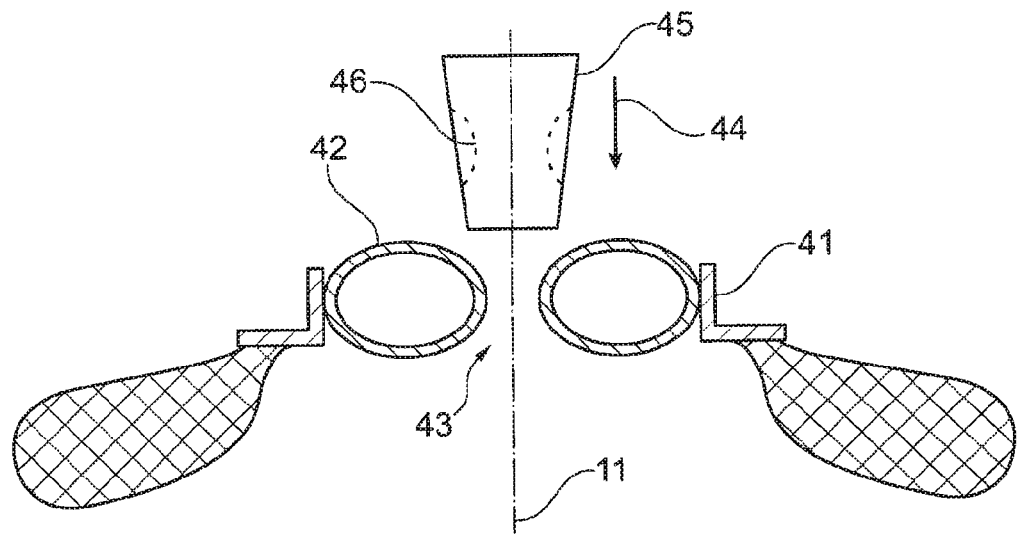
FIG. 10 shows a connecting device with a hollow ring seal and a dowel that can be inserted thereinto for expansion.
Figure 11:
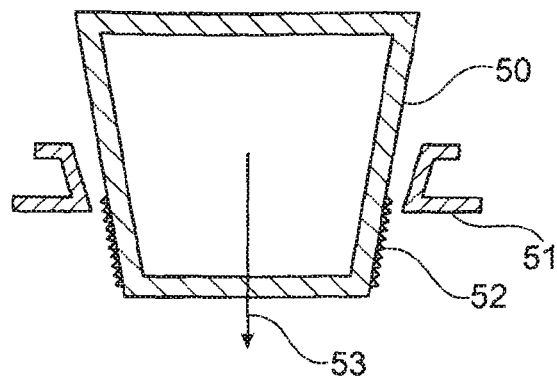
FIG. 11 shows a connecting device with a conical stopper, which can be pushed directly into the opening of the suture ring.
Figure 12:
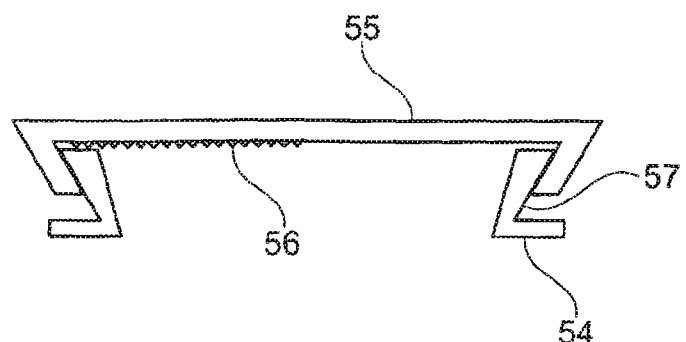
FIG. 12 shows a connecting device with a stopper, which is clamped radially outwardly onto an outer face of the suture ring.

The innovation will be presented and explained hereinafter on the basis of exemplary embodiments in figures of a drawing, in which FIG. 1 shows a schematic section of a connecting device with a ring seal, which serves as a securing element and as a sealing element, FIG. 2 shows a connecting device with a hollow ring seal, FIG. 3 shows a connecting device with an elastic cover, FIG. 4 shows a connecting device with a cover that has elastic hooks, FIG. 5*a* shows, in a half-section, a connecting device with a cover and a cap nut, FIG. 5*b* shows a spring ring as a detail from FIG. 5*a*, FIG. 6 shows, in section, a connecting device with a hollow rubber body, FIG. 7 shows a connecting device with a hollow rotatable rubber body, FIG. 8 shows a connecting device with a hollow sealing element and an expansion device, FIG. 9 shows a connecting device with a valve, on the right-hand side with an inserted pump pipe, FIG. 10 shows a connecting device with a hollow ring seal and a dowel that can be inserted thereinto for expansion, FIG. 11 shows a connecting device with a conical stopper, which can be pushed directly into the opening of the suture ring, and FIG. 12 shows a connecting device with a stopper, which is clamped radially outwardly onto an outer face of the suture ring.

FIG. 1, in a section, schematically shows a connecting device 1 for connecting a pipe or tube-shaped element to the heart of a patient. The connecting device 1 comprises a suture ring 2, which itself comprises a hard part 3, formed as a metal ring, and a softer region 4, which can be sewn to organic tissue 5, for example of a patient's heart, by means of a needle and thread. The region 4 can be formed for example as a textile fabric.

The suture ring 2 has a central cylindrical opening 6, through which, during operation of a heart pump, a pipe, a cannula or a tube can be guided and is usually sealed there. In the depiction of FIG. 1, this opening 6 is closed tightly by means of a closure element 7. The closure element 7 comprises two elements 8, 9 that can be pressed against one another, which are each formed cylinder-symmetrically, and which are formed in a disc-like manner in the radially inner part. The two elements 8, 9 have bevels 8*a*, 9*a* in the radially outer region, which bevels face towards one another, run around the periphery of the suture ring and together form a groove 8*a*, 9*a* having V-shaped side walls, in which a sealing ring 10 lies. If the two elements 8, 9 are pressed against one another in the axial direction 11, which corresponds to the through-direction of the opening 6 and the conveying direction of a liquid when the connector is open, the sealing ring 10 is compressed in the axial direction and thus pressed in the radial direction against the inner wall of the metal part 3 of the suture ring 2. The closure element 7 is thus clamped tightly in the suture ring 2.

In order to ensure an axial compression of the elements 8, 9, a threaded bolt 12 is connected to the element 8 and protrudes through a central opening in the element 9, and a threaded nut 13 can be screwed onto said threaded bolt 12. The element 9 comprises a rim 14, which protrudes beyond the edge of the metal part 3 of the suture ring 2. As the closure element 7 is manipulated, a surgeon for example can grasp the closure element at the rim 14 and can turn the threaded nut 13 in order to press the elements 8, 9 against one another or to release them from one another as the nut 13 is loosened. The actual suture ring 2 does not necessarily have to be grasped by the surgeon as the closure element 7 is attached and released, and the forces acting on the suture ring 2 are limited during the closure or release process. The risk that the soft part 4 of the suture ring 2 detaches from the organic tissue 5 of the heart wall is thus minimised.

The sealing ring 10 can consist for example of rubber or a silicone elastomer and in cross-section can assume almost any forms, which have to be matched only to the form of the groove 8*a*, 9*a*, which is formed between the elements 8, 9. Favourable cross-sections for example can be triangular, circular, or elliptical.

FIG. 2 shows a suture ring 2', into which a closure element 7' is inserted. The closure element 7' comprises two elements 8', 9' that can be axially pressed together, which, as in FIG. 1, can be pressed together and released by means of a combination of a threaded bolt 12' and a threaded nut 13'. An annular, hollow elastomer element 10' is provided as sealing element and expands radially outwardly under compression of the elements 8', 9' and seals against the inner wall 15 of the metal part 3' of the suture ring 2'.

Alternatively, spring clips 16, 17 are indicated in a dashed manner as an alternative and can be provided additionally to, or instead of the compression mechanism consisting of the threaded bolt 12' and the nut 13', in order to axially compress the elements 8', 9'.

In addition, another mechanism is also shown in FIG. 2, which mechanism leads to a sealing of the sealing element 10' against the inner wall 15 of the suture ring 2', specifically the introduction of a substance, for example a gas, a gel, or a liquid, into the cavity of the sealing element 10' by means of an injection mechanism 18, which in the simplest case can be embodied by an injection syringe. In order to seal the closure element 7' against the suture ring 2', gas or a gel or a liquid can then be introduced into the sealing element 10' by means of a syringe via a needle piercing said sealing element 10', in order to expand the sealing element 10'. On account of an absence of expansion possibilities in the axial direction, the sealing element 10' is expanded radially outwardly and seals against the suture ring 2'. In addition, it can be provided in a method step that the substance is solidified in the cavity of the sealing element 10', for example by cross-linking as a result of thermal treatment or irradiation, and that the closure element is thus fixed in the suture ring 2'.

FIG. 3 shows a closure mechanism with a closure element 7" in the form of an elastic cover, which can be snapped onto the solid region 3" of the suture ring 2". The closure element 7" can be formed for example in such a way that it has two stable dimensional states, between which it can be moved, wherein in one stable dimensional state the closure element can be snapped over the edge of the metal part 3" and a rib 19 running peripherally around said part. The closure element 7" comprises an inwardly curved peripheral rim 47 in order to hook beneath the rib 19. The round cover 7" forms the closure element itself and also the elastic securing element and also the sealing element.

The elastic cover 7" can consist of a textured material, for example a surface-textured metal, for example titanium, a metal foam, a textile, or fabric, which promotes ingrowth. Here, it is also conceivable that the cover is made tight only as a result of the ingrowth. The texturing or covering with a textile or fabric is denoted in FIG. 2 by 49. In addition, the cover, on its side facing towards the suture ring, can comprise a ring seal 48 made of an elastomer or for example also having a textured surface.

FIG. 4, in section, shows a connecting device with a suture ring 2''' and a closure element 7*m*, wherein the metal part 3''' of the suture ring has an outer peripheral rib 19 similar to the rib 19 of FIG. 3, wherein, however, in the exemplary embodiment of FIG. 4 it is not a peripheral rim 47 that is deformed and hooked on the peripheral rib 19, but instead merely individual elastic hooks 20, 21, which can each be deflected radially at their free end and carry there a hook 20*a*. The closure element 7''' here itself constitutes the sealing element, which seals against the metal part 3''' of the suture ring. The securing elements are formed in this example by the elements 20, 20*a*, 21. In particular, it is possible to attain a long-term sealing effect in that the growth of tissue is promoted with a texture 49' made of metal or textile on the inner faces of the closure element. An additional seal is thus attained by tissue.

FIG. 5*a* shows a half-section of a suture ring with a soft region 4'''' and a metal region 3'''', in which a closure element 7'''' is placed. The closure element 7'''' comprises a spring ring 22, which can be placed around a pipe connection-like part of the metal part 3'''' and can be hooked there behind a rib 19. A cap nut 23 can be attached to the spring ring 22, which is shown separately in FIG. 5*b* in a perspective view and is slitted for the elastic expandability, which cap nut can be connected or is fixedly connected to a round cover 24 of the closure element 7''''. In order to close the connecting device, the spring ring 22 is thus firstly elastically laid or clamped over the metal part 3'''' of the suture ring, and the cap nut 23 is then screwed on, with the cover 24.

The closure elements 25, 26 shown in FIGS. 6 and 7 each have a pot-like body 25*a*, 26*a* consisting of an elastomer, with a base 25*b*, 26*b* and a cylindrical wall part 25*c*, 26*c* and a pillar 25*d*, 26*d* fixedly connected to the base 25*b*, 26*b* respectively. In order to introduce and release the closure elements 25, 26 in the openings in the respective suture rings in FIGS. 6 and 7, the pillars 25*d*, 26*d* can be rotated relative to the pot-like bodies 25*a*, 26*a* about the axis 11. As a result of this relative movement between the pillars and the pot-like bodies, each of the pot-like bodies 25*a*, 26*a* collapses radially and releases from the sealing face at the corresponding suture ring. If the relative rotation between the pillars and the pot-like bodies is undone, the pot-like bodies 25*a*, 26*a* expand radially, until they are placed again in a sealing manner against a cylindrical sealing face of the corresponding suture ring.

The pot-like bodies 25*a*, 26*a* have one or more radial extensions 25*e*, 25*f* and 26*e* for fixing to the corresponding suture ring, which extensions each form stops on one or both sides of the suture ring in the axial direction and thus prevent the closure elements 25, 26 from sliding out from the opening of the corresponding suture ring in the axial direction.

The pillars 25*d*, 26*d* for example can comprise thickened portions as shown in FIG. 7, in order to allow an improved grip for rotation.

Resilient support elements in the form of wire rings can be incorporated within the pot-like bodies 25*a*, 26*a*, integrated in a wall of the corresponding body, which support elements act elastically towards the reestablishment of the expanded state in the event that a torsional force is cancelled. A body of this kind in the form of a round wire ring 27 is shown by way of example in FIG. 7.

FIG. 8 shows a closure element 28, which comprises a hollow sealing element 29, for example in the form of a balloon-like body formed of an elastomer, wherein plate-like regions 29*a*, 29*b* are arranged symmetrically opposite one another and are connected to one another by a cylindrical wall region 29*c*. The plate-like regions 29*a*, 29*b* have a rigidity that causes the plate-like regions to be flattened and simultaneously radially expanded in the event that said regions ore moved axially closer to one another along the axis 11. In accordance with FIG. 8, a spindle 30 is provided, which is guided in a guide 31 joined to the upper plate-like region 29b. A spindle nut 32 is secured centrally in the plate-like region 29a and cooperates with the spindle 30. If the spindle 30 is rotated by means of its head 33 fixedly connected thereto, the distance between the spindle nut 32 and the head 33 is thus reduced or increased depending on the direction of rotation, and the sealing element 29 is consequently radially expanded or compressed. The wall region 29c can thus seal against a sealing face of the suture ring 34 in the event that the sealing element 29 is radially expanded.

FIG. 9, in a sectional illustration, shows a closure element 35, which comprises a pipe connection 35a, which is guided through a suture ring 36 until a flange 37 rests on the suture ring. The pipe connection 35a, on its inner side, has one or more flexible elastic pivot elements 38, which for example can each form a segment of a circular disc and which in the relaxed state close the opening 39 of the pipe connection 35a in the manner of a valve.

If a pump pipe 40 or a tube-shaped or cannula-like object is to be inserted through the opening 39, the pivot elements 38 thus retreat and make space for the inserted object, as shown in the right-hand part of the illustration of FIG. 9 to the right of the central axis 11.

Parts of the pipe connection 35a, in particular on the outer side thereof, can have a textured metal surface, in particular a textured titanium surface, which promotes cell growth after implementation in a living organism and thus accelerates the ingrowth and also the seal provided by living tissue. A texturing of this kind can also be provided on the solid, in particular metal parts of the closure elements already described above, in order to facilitate or accelerate the ingrowth after insertion into a patient's body.

FIG. 10 shows, within a suture ring 41, a hollow sealing element 42 in the form of a hollow elastomer torus, in the axial opening 43 of which a conical stopper 45 can be inserted along the axis 11 in the direction of the arrow 44. The stopper 45 is elastically clamped and held in the opening 43 and can have an indentation 46, shown in a dashed manner in FIG. 10, for improved fixing. By means of the insertion of the stopper 45 into the sealing body 42, said sealing body is radially expanded and seals against the cylindrical inner face of the suture ring 41.

FIG. 11 shows a suture ring 51, which itself has a conical inner contour, but can also have a cylindrical inner contour. A conical stopper 50 can be hollow and can consist of a plastic, elastomer or a metal, also a foamed metal, an open-pore metal structure, and in particular titanium. The stopper can be gas-filled and is pressed axially into the opening of the suture ring in the direction of the arrow 53. The stopper can be textured at least in part at its periphery, in particular in the sealing region, on its surface, or can be coated with a textured substance, in order to promote ingrowth (see reference sign 52).

FIG. 12 shows a suture ring 54, which has a conical outer contour 57, onto which there is clamped a peripheral rim of the elastic closure element 55, in order to seal either there in the region of the lateral surface of the suture ring or at the end face thereof. The closure element 55 can be provided wholly or partially with a texturing 56 or for example can consist of an open-pore metal structure or a metal foam or metal fabric.

The implementations of the innovation defined in the claims and presented on the basis of the exemplary embodiments allow the opening of a suture ring to be closed whilst avoiding excessive movements or applications of force on the suture ring, such that closure by means of a closure element is made possible without endangering the patient and with minimal impact.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A connecting device for connecting a pipe or tube-shaped element to a heart or a blood vessel of a patient, the connecting device comprising:
   a suture ring that has an opening, which is closable by means of a closure element and through which said pipe or tube-shaped element is guided in the axial direction, wherein the closure element is secured to the suture ring by means of at least one elastic securing element, wherein the closure element is movable between two stable dimensional states, wherein in one stable dimensional state, of the closure element can be snapped over a peripheral rib of the suture ring.

2. The connecting ring according to claim 1, wherein the closure element includes a sealing element, and wherein the sealing element is compressible in the axial direction and thus is expandable in the radial direction.

3. The connecting device according to claim 1, wherein the closure element includes a sealing element, and wherein the closure element has a peripheral recess at its periphery for the sealing element compressible in the axial direction.

4. The connecting device according to claim 1, wherein the closure element includes a sealing element, and wherein the sealing element is an elastomer seal.

5. The connecting device according to claim 4, wherein the sealing element has a circular, oval, triangular, quadrangular, annular, pot-shaped, or polyhedral cross-section, and is hollow and consists of a foam material or metal foam.

6. The connecting device according to claim 1, wherein the closure element can be clamped elastically in a sealing manner onto an outer contour of the suture ring.

7. The connecting device according to claim 1, wherein the closure element includes a sealing element, and wherein the closure element and/or the securing element and/or the sealing element respectively, wholly or partially on its surface, has a texturing or is covered by a textured layer.

8. The connecting device according to claim 7, wherein the texturing or the textured layer is in the form of a textile or fabric, and the closure element and/or the securing element and/or the sealing element consist/consists of a metal, an open-pore metal structure or a metal foam, of titanium, plastics material, an open-pore textile fabric, or an organic foam material.

9. The connecting device according to claim 1, wherein the closure element is configured to exert a radially inward clamping force on a radially outward contour of the suture ring such that it is elastically clamped onto the suture ring in a sealing manner.

10. The connecting device according to claim 1, wherein the closure element comprises an inwardly curved peripheral rim configured to hook beneath the peripheral rib of the suture ring.

11. The connecting device according to claim 1, wherein the elastic securing element is formed by the closure element.

* * * * *